US00PP30204P2

(12) United States Plant Patent
Korlipara

(10) Patent No.: US PP30,204 P2
(45) Date of Patent: Feb. 12, 2019

(54) ***ECHINACEA* PLANT NAMED 'TNECHPR'**

(50) Latin Name: ***Echinacea* spp.**
Varietal Denomination: TNECHPR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,024

(22) Filed: Jan. 25, 2018

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'TNECHPR' is provided herein, characterized by red ray florets, an amazing number of inflorescences starting in the first season, a very compact habit, very long bloom time with excellent rebloom, ray florets held horizontally, and excellent vigor.

1 Drawing Sheet

Botanical denomination: *Echinacea* spp.
Variety designation: 'TNECHPR'.
Trademark designation: Prima™ Ruby.

BACKGROUND OF THE INVENTION

The present invention relates to a new and distinct cultivar of *Echinacea* and given the cultivar name 'TNECHPR'. *Echinacea* is in the family Asteraceae. The new cultivar is part of a planned breeding program for a landscape series with very compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Balsomsed', U.S. Plant Pat. No. 23,105, the new cultivar is shorter and has inflorescences that are larger.

Compared to *Echinacea* 'Dixie Scarlet', U.S. Plant Pat. No. 26,110, the new cultivar is shorter with more ray florets that are a deeper red color.

Compared to *Echinacea* 'TNECHKR', U.S. Plant Pat. No. 28,768, the new cultivar is shorter.

This new *Echinacea* cultivar is uniquely distinguished by:

1. red ray florets,
2. an amazing number of inflorescences starting in the first season,
3. a very compact habit,
4. very long bloom time with excellent rebloom,
5. ray florets held horizontally, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Echinacea* 'TNECHPR' growing in the trial field in full sun in early September in Canby, Oreg.

DETAILED PLANT DESCRIPTION

The following is a detailed description of the new *Echinacea* cultivar based on observations of 9-month-old specimens growing in the trial field in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type*.—Herbaceous perennial.
*Hardiness*.—USDA Zones 4 to 9.
*Size*.—Grows to 36 cm wide and 40 cm tall to top of inflorescences.
*Form*.—Basal clump, with 1 to 8 stems from the base.
*Vigor*.—Excellent.
*Roots*.—Fibrous, with many downward growing and few laterals, ivory in color, Yellow White 158D, roots develop easily from cuttings from the crown.

Leaf (stem):

*Type*.—Simple.
*Shape*.—Lanceolate.
*Arrangement*.—Alternate.
*Blade size*.—Grows to 10 cm long and 3 cm wide.
*Margins*.—Entire to sparsely serrate.
*Apex*.—Acuminate.
*Base*.—Attenuate.
*Surface texture*.—Strigose on both sides.

*Venation*.—Pinnate, Yellow Green 145C on both sides.

*Color*.—Topside Green N137B, bottom side closest to Yellow Green 147B.

*Petiole description*.—Clasping, grows to 5 cm long and 3 mm wide, scabrous, narrow leafy edges which fold upwards, Yellow Green 146C.

Inflorescence:

*Type*.—Composite on terminal stalked heads.

*Flowering stem*.—Grows to 36 cm tall from the base of the plant to the terminal inflorescence and can grow to 13 cm long from the top stem leaf to the base of an inflorescence; unbranched to branched, with 1 to 5 inflorescences per stem; diameter growing to 6 mm wide near the inflorescence; strigose; Yellow Green 146C in shade and tinted Greyed Purple 187B in sun.

*Size*.—Grows to 10 cm wide and 7 cm deep as disc enlarges.

*Form*.—Ray florets held horizontally, curving down in old inflorescences, mature disc is conic.

*Immature inflorescence* (*bud*).—3.5 cm wide and 2 cm deep, ray florets held upright at 30 degree angle and rolled up so only the back color shows, Red Purple 60A, disc color Greyed Purple 187A.

*Ray florets*.—Without pistil or stamen, 29 to 37 in number, grow to 42 mm long and 10 mm wide, oblanceolate with the tip two-toothed (each acute), entire margins, base attenuate, glabrous on both sides; fully open florets topside Red 46A, bottom side Red 38B with streaks of Greyed Purple 185B; florets fade gradually to both sides Greyed Purple 185A with Greyed Orange 175B at base.

*Disc*.—Flat becoming conic, becoming 38 mm deep and 40 mm wide with maturity, Greyed Purple N186B.

*Disc florets*.—About 400 in number, each with 1 pistil and 4 stamen, grow to 10 mm long and 2 mm wide, each with one persistent, very stiff linear bract (15 mm long with the top 1 mm Greyed Purple N186B, blending to 3 mm Greyed Purple 187A, blending to 3 mm Green 137A blending to White NN155A on bottom); corolla 7.5 mm long and 2 mm wide, tubular, 5 lobed, glabrous, Greyed Purple N186C on tips blending to Yellow Green 147B at base; pistil 11 mm long, ovary 3 mm long, White NN155D with top Yellow Green 144A, style 7 mm long Yellow Green 149D, 2-branched stigma spreading 2.5 mm wide, Greyed Purple 187B; stamen 6 mm long, filaments 2 mm long and White NN155B, anthers 4 mm long and Greyed Purple N186A, pollen, moderate, Yellow Orange 19A.

*Involucral bracts*.—In 4 leafy series, area grows to 32 mm wide and 5 mm deep, lobes lanceolate in shape, reflexed and curl back, grow to 13 mm long and 3 mm wide, Green N137A, margins strigose, tip acute, strigose on both sides.

*Receptacle*.—Grows to 10 mm wide and 20 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: 3 mm long and 2.5 mm wide, oval, Brown 200C.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

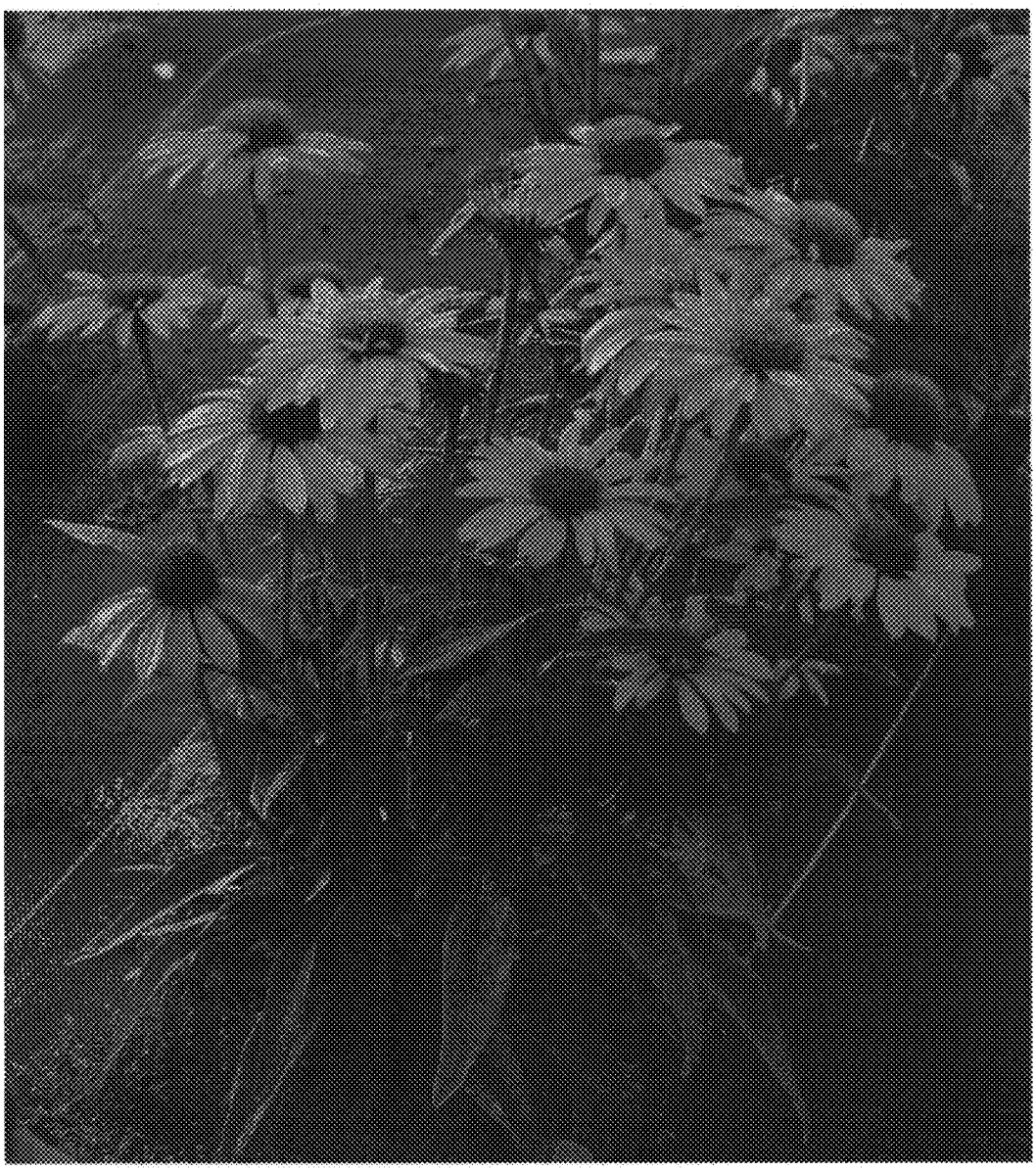

* * * * *